United States Patent
Pastor et al.

(10) Patent No.: US 7,361,755 B2
(45) Date of Patent: Apr. 22, 2008

(54) TRANSITION-METAL-CATALYZED PROCESS FOR THE CONVERSION OF ALKENES TO STERICALLY HINDERED SUBSTITUTED N-ALKOXYAMINES

(75) Inventors: Stephen Daniel Pastor, Mayhill, NM (US); Sai Ping Shum, Jamesburg, NJ (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 481 days.

(21) Appl. No.: 10/499,954

(22) PCT Filed: Dec. 12, 2002

(86) PCT No.: PCT/EP02/14134

§ 371 (c)(1),
(2), (4) Date: Jun. 21, 2004

(87) PCT Pub. No.: WO03/053931

PCT Pub. Date: Jul. 3, 2003

(65) Prior Publication Data

US 2005/0085636 A1    Apr. 21, 2005

Related U.S. Application Data

(60) Provisional application No. 60/409,374, filed on Sep. 9, 2002, provisional application No. 60/342,330, filed on Dec. 21, 2001.

(51) Int. Cl.
- *C11C 5/00* (2006.01)
- *C07D 265/00* (2006.01)
- *C07D 405/00* (2006.01)
- *C07D 211/00* (2006.01)

(52) U.S. Cl. .................. 544/1; 544/63; 544/224; 546/187; 546/189; 546/191; 548/100; 548/146; 548/215; 548/240; 548/400; 548/517; 548/525; 564/300

(58) Field of Classification Search .......... 544/1, 544/63, 224; 548/100, 146, 215, 240, 400, 548/517, 525; 546/187, 189, 191; 564/300
See application file for complete search history.

(56) References Cited

U.S. PATENT DOCUMENTS

| | | | |
|---|---|---|---|
| 4,082,810 A * | 4/1978 | Brown | 568/6 |
| 4,921,962 A | 5/1990 | Galbo et al. | 546/184 |
| 6,271,377 B1 | 8/2001 | Galbo et al. | 546/14 |
| 6,547,841 B2 * | 4/2003 | Pastor et al. | 44/275 |
| 6,579,328 B2 * | 6/2003 | Pastor et al. | 44/275 |
| 6,841,668 B2 * | 1/2005 | Judd et al. | 544/53 |
| 2003/0171461 A1 | 9/2003 | Hafner et al. | 524/99 |
| 2003/0208071 A1 | 11/2003 | Judd et al. | 544/207 |

OTHER PUBLICATIONS

Ollivier et al., Synlett, No. 6, (1999), pp. 807-809.
Ciba Specialty Chemicals Corp., U.S. Appl. No. 10/496,773, filed Nov. 19, 2002.
Ciba Specialty Chemicals Corp., U.S. Appl. No. 10/889,339, filed Jul. 12, 2004.
H. Brown et al., J. Am. Chem. Soc., vol. 82, (1960), pp. 4708-4712.
J. Org. Chem., vol. 22, (1957), p. 1136-1137.
J. Am. Chem. Soc., vol. 83, (1962), pp. 1001-1002.
Bawn et al., J. Chem. Soc., (1960), pp. 3923-3925.
G. Whitesides et al., Journal of the American Chemical Society, vol. 96, No. 9, (1974), pp. 2806-2813.
Organic Syntheses via Boranes, Wiley and Sons, NY, (1975), pp. 17-18.
Y. Chujo et al., Macromolecules, (1993), vol. 26, pp. 2643-2644.

* cited by examiner

*Primary Examiner*—Janet L. Andres
*Assistant Examiner*—Raymond Covington
(74) *Attorney, Agent, or Firm*—Tyler A. Stevenson

(57) ABSTRACT

This invention pertains to a novel process for preparing sterically hindered N-substituted alkyloxyamines from alkenes by the transition-metal-catalyzed reaction of a intermediate alkylborane with a sterically hindered nitroxyl radical.

9 Claims, No Drawings

TRANSITION-METAL-CATALYZED PROCESS FOR THE CONVERSION OF ALKENES TO STERICALLY HINDERED SUBSTITUTED N-ALKOXYAMINES

This is a 371 of international application PCT/EP02/14134, filed Dec. 12, 2002, which claims benefit of U.S. provisional application Nos. 60/409,374, filed Sep. 9, 2002 and 60/342,330, filed Dec. 21, 2001.

This invention pertains to a novel process for preparing sterically hindered N-substituted alkyloxyamines from alkenes by the transition-metal-catalyzed reaction of an intermediate alkylborane with a sterically hindered nitroxyl radical.

BACKGROUND OF THE INVENTION

N-alkoxyamines derivatives of sterically hindered amines are prepared generally from the corresponding amines or the N-oxyl derivatives using a hydroperoxide in the presence of a small amount of a metal ion catalyst in a hydrocarbon organic solvent as described in U.S. Pat. No. 4,921,962.

An alkyl borane is generally prepared by the hydroboration of an alkene with borane as described by H. C. Brown, *J. Am. Chem. Soc.*, 82,1960, p4708-4712; *J. Org. Chem.*, 22, 1957, p1136; Organic Synthesis via boranes, Wiley and Sons, NY, 1975, p 17-18. In addition, Brown also described the coupling (yield <70%) of a hydroborated alkene in situ by stoichiometric amount of silver nitrate in the presence of alkali, *J. Am. Chem. Soc.*, 83, 1962, p1001; *J. Am. Chem. Soc.*, 83,1962, p1002. Brown proposed that the aforementioned reaction is the coupling of alkyl radicals generated by a silver alkyl. The kinetics of the decomposition of the silver alkyls is also studied by C. E. H. Bawn, *J. Chem Soc.*, 1960, 3923; Further evidence is observed by G. M. Whitesides where n-alkyl(tri-n-butylphosphine)silver (I) can be thermally decomposed to give alkyl radicals which is subsequently trapped by stoichiometric 2,2,6,6-tetramethylpiperidine-1-oxyl (TEMPO) in moderate to poor yield (65%); *J. Am. Chem. Soc*, 96,1974, p 2806-2813.

The instant invention provides a novel process for the preparation of sterically hindered alkoxyamines in a non-oxidative reaction medium. This allows a variety of functional groups on the starting N-oxyl derivatives without the need of protection (4-keto or 4-hydroxy-TEMPO give corresponding N-ethoxy product in >95% yield). Furthermore, the instant invention can produce primary alkoxyamine derviatives which is not possible in the sited hydroperoxide process.

The instant invention also provides corresponding products in very high to nearly stoichiometric (>90%) yield at low temperature. Unlike the sited references, the instant process can be operated from stoichiometric to a 1% molar catalytic system along with significant higher yields than sited. In addition, the instant process can be operated in an alcoholic or aqueous medium at ambient temperature which is not operative as described by Whitesides.

The instant invention allows the facile synthesis of N-alkyloxy hindered amines from alkenes which are gases, for example, an N-ethyloxy hindered amine from ethene.

DETAILED DISCLOSURE

The instant invention pertains to a process for preparing a sterically hindered amine of formula I, II, III, IV, V or VI

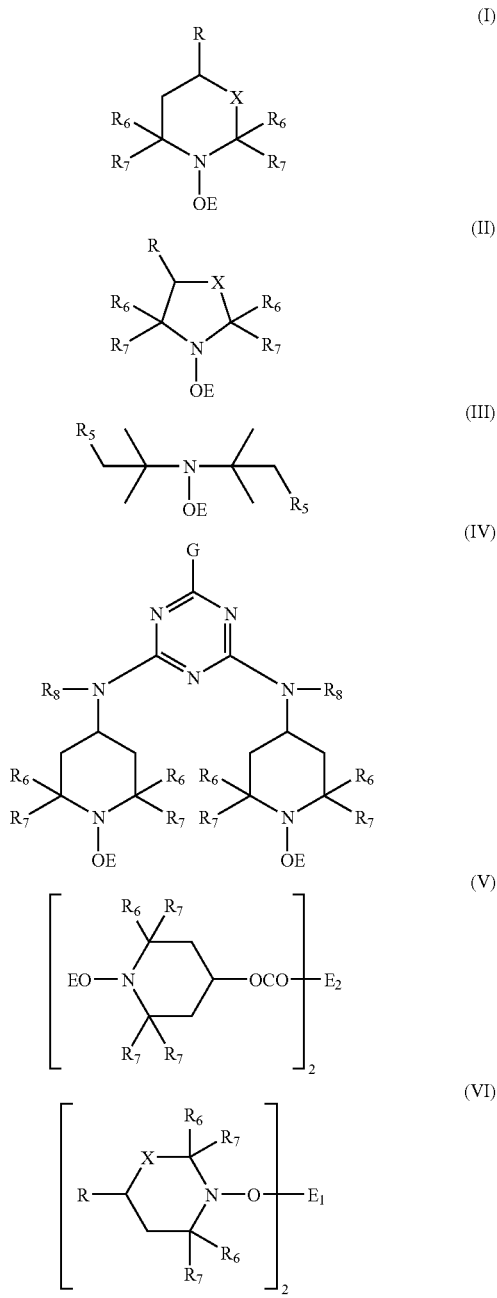

which process comprises reacting a corresponding sterically hindered nitroxyl compound of formula Ia, IIa, IIIa, IVa or Va

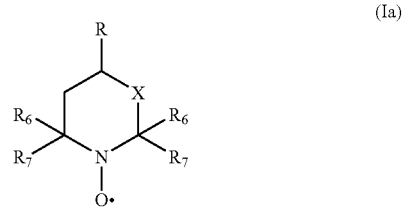

-continued (IIa)

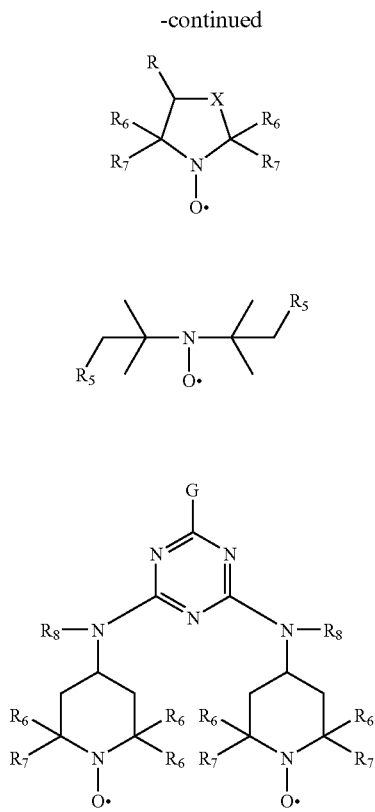

(IIIa)

(IVa)

(Va)

with an alkylborane of formula

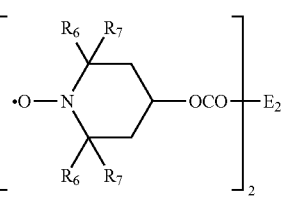

or reacting two equivalents of the sterically hindered nitroxyl of formula Ia with a cyclic or bis alkylborane of formula

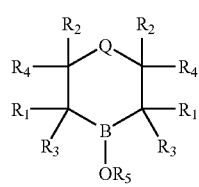

-continued
or

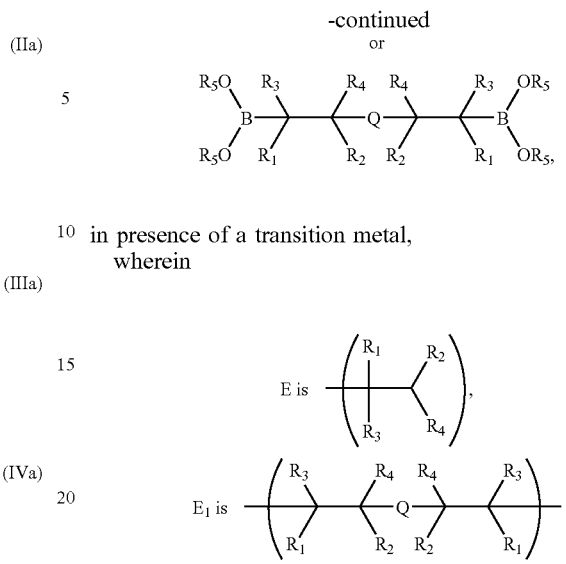

in presence of a transition metal,
wherein

E is 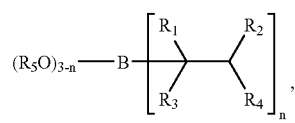, $E_1$ is (shown above)

n is 1 to 3,

R is hydrogen, alkyl of 1 to 18 carbon atoms, aralkyl of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, $R_1$ to $R_4$ are independently hydrogen, halogen, alkyl of 1 to 18 carbon atoms, aralkyl of 7 to 15 carbon atoms, aryl of 6 to 10 carbon atoms, alkylthio of 1 to 18 carbon atoms, alkoxy of 1 to 18 carbon atoms, aryloxy of 7 to 15 carbon atoms, or $R_1$ and $R_2$ together with the carbon atoms to which they are attached form a cycloalkylene of 5 to 18 carbon atoms or said cycloalkylene interrupted by 1 to 3 nitrogen, oxygen or sulfur atoms; or said cycloalkylene substituted by 1 to 3 halogen, alkyl of 1 to 18 carbon atoms, aralkyl of 7 to 15 carbon atoms, aryl of 6 to 10 carbon atoms, alkylthio of 1 to 18 carbon atoms, alkoxy of 1 to 18 carbon atoms or aryloxy of 7 to 15 carbon atoms, $R_5$ is hydrogen, alkyl of 1 to 18 carbon atoms, cycloalkyl of 5 to 12 carbon atoms, aralkyl of 7 to 15 carbon atoms or aryl of 6 to 10 carbon atoms, $R_6$ and $R_7$ are independently alkyl of 1 to 8 carbon atoms, or $R_6$ and $R_7$ together are tetramethylene or pentamethylene, X is —$CH_2$—, —O—, —S—, or —$NR_8$—, $R_8$ is hydrogen or alkyl of 1 to 12 carbon atoms, Q is a direct bond or is methylene of 1 to 12 carbon atoms or said methylene interrupted by 1 or 2 nitrogen, oxygen or sulfur atoms, $E_2$ is alkylene of 2 to 12 carbon atoms and G is chloro or —N(2-ethylhexyl)$_2$.

Halogen is for example chloro, bromo and iodo.

Alkyl is a straight or branched chain of for example 1 to 30 carbon atoms, for instance, 1 to 18 carbon atoms or 1 to 12 carbon atoms, and is for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

Cycloalkyl groups are for example of from 5 to 12 carbon atoms and include cyclooctyl, cyclohexyl, cyclopentyl, cyclodecyl, norbornyl, 3-methylcyclohexyl and 4-methylcyclohexyl; typical cycloalkenyl groups include cyclohexenyl.

Cycloalkylene is a divalent cycloalkyl group as defined herein. A cycloalkylene interrupted by a heteroatom is for example 3-pyranyl.

Aralkyl groups are for example of 7 to 9 carbon atoms and include benzyl, alpha-methyl-benzyl, alpha, alpha-dimethylbenzyl or phenethyl.

Aryl is for instance phenyl, napthyl and biphenyl.

Alkoxy and aryloxy groups are defined as for the present alkyl and aryl groups.

Where Q is a direct bond, the group $E_1$ may be derived from for example dipentene (limonene) or 1,3-butadiene. The hindered amines of formula VI are produced from the reaction of two equivalents of nitroxyls of formula Ia with a cyclic or bis alkylborane. It is also comtemplated that nitroxyls of formula IIa-Va may likewise be reacted with cyclic or bis alkylboranes of this invention to produce bridged products.

Styrenes are a suitable alkyene for the present process, for example styrene or α-methylstyrene.

Indeed, the instant compounds can be made directly from nitroxides which are commercially available such as TEMPO (1-oxyl-2,2,6,6-tetramethylpiperidine), 4-OXOTEMPO (1-oxyl-2,2,6,6-tetramethyl-4-oxopiperidine) and di-tert-butyl nitroxide.

In the instant invention, an alkene is converted. to a NOR HALS by the transition-metal-catalyzed reaction of an intermediate alkylborane with a stable nitroxyl readical. The alkylborane can be isolated or bepared in situ by any number of known methods. In general, prior free radical methods (cite Winter patent) gives mixtures of isomers. The instant invention tends in many cases to give a single isomer which was previously unavailable. For example, the process of the instant invention with tri-n-octylborane with 4-hydroxy-2,2,6,6-tetramethylpiperidine-1-oxyl gives a NOR HALs with predominate amount of the product where the oxygen of the NOR is bonded to a primary carbon atom of the octane. Prior free-radical processes give a mixture of NO-octyl isomers where the oxygen is predominantly bonded to secondary carbon atoms. The selectivity in the instant invention has an advantatage in isolation and purification of the products, as well as simplifying toxicological studies of the product in end use areas. Furthermore, the non-oxidative method of the instant invention minimizes by-products as a result of non-selective oxidation in other free radical processes.

The transition-metal catalyst of the instant invention mainly belongs to group 10 or 11 (also known as I0 and IB), for example silver and gold. The transition-metal metal may be used in about stoichiometric or catalytic quantity. When used in about stoichiometric amount, the metal is, for example, used in an amount from about 50 mole % to about 200 mole % relative to the amount of nitroxyl compound (formulae Ia, IIa, IIIa, IVa, Va) present. When used catalytically, the metal is preferably used at 5 to 0.1 mole % of stoichiometric quantity (i.e. relative to the amount of nitroxyl compound), for example, about 5 mole %, or about 1 mole % (e.g. in the range 0.1 to 2 mole %), and in the presence of a Cu(II)/oxygen co-catalyst.

The copper (II)/oxygen co-catalyst comprises $Cu^{2+}$ and oxygen. The copper (II) part of the co-catalyst is preferably a copper (II) salt such as copper (II) acetate or copper (II) sulfate. The co-catalyst keeps the transition metal, e.g. the silver or gold, in the appropriate oxidation state for the reaction. The oxygen part of the co-catalyst may be introduced as a static oxygen blanket or introduced directly into the reaction mixture. The oxygen may be introduced as atomspheric oxygen or a mixture of oxygen with another inert gas or gases. The Cu(II) is mainly used between 0.1 and about 5 mole percent, preferable 5 mole percent.

Upon completion of the reaction, the transition metal, e.g. silver metal, precipitates from solution and may be recovered.

The solvent is for example water, a mixture of water and tetrahydrofuran, alcohol, a mixture of alcohol and tetrahydrofuran or a mixture of water and alcohol. Alcohol is for example methanol, ethanol and propanol.

The process may conveniently be carried out between about 0 and about 100 degrees C, preferably between about 20 to about 40 degrees C.

The instant invention also pertains to a composition stabilized which comprises (a) an organic material subject to degradation by heat, light or oxygen, and (b) an effective stabilizing amount of a compound of formula I, II III, IV, V and/or VI as described above.

For example, the organic material is a natural, semi-synthetic or synthetic polymer, especially a thermoplastic polymer.

In another embodiment, the polymer is a polyolefin or polycarbonate; for example, polyethylene or polypropylene; or is polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalenedicarboxylate), or other blends or copolymers such as poly(ethylene/1,4-cyclohexylenedimethylene terephthalate) PETG or an ionomer as described on page 29.

In another embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

For example, the resin is a thermoset acrylic melamine resin or an acrylic urethane resin.

In yet another embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula I, II III, IV, V, VI can be incorporated into the carder material as early as the production of the latter, in the production of paper, for example, being added to the paper pulp. A second method of application is to spray the carder material with an aqueous solution of compounds of formula I, II III, IV, V and/or VI, or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula I, II III, IV, V, VI can be easily incorporated into the coating composition.

The recording material according to this invention contains 1 to 5000 mg/m$^2$; or 50-1200 mg/m$^2$, of a compound of formula I, II, III, IV, V and/or VI.

As already mentioned, the recording materials according to the invention embrace a wide field. The compounds of formula I, II III, IV, V or VI can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula I, II III, IV, V or VI act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula I, II III, IV, V or VI can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophoto-graphic printers and pen-plotters. Of the above, recording materials for dye diffusion transfer printing are useful, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

In general polymers which can be stabilized include

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene. (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EM and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl; vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrenelisoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloridelvinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4, -trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenovformaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5-15% by weight of the instant compounds. Concentrations of 5-10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated Monophenols, for Example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(□-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated Hydroquinones, for Example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated Thiodiphenyl Ethers, for Example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-Bisphenols, for Example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl Compounds, for Example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for Example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic Acid with Monohydric or Polyhydric Alcohols, for Example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic Acid with Monohydric or Polyhydric Alcohols, for Example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic Acid for Example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for Example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonylethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2', 4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyldiethanolamine, nickel dibutyidithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl) ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide; 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para- methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenyl-propionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyinitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Amine Oxides, for example, tridecyl amine oxide, tridodecyl amine oxide, trihexadecyl amine oxide, tri($C_{12}$-$C_{14}$ alkyl) amine oxide, tri($C_{16}$-$C_{18}$ alkyl) amine oxide, tri($C_{20}$-$C_{22}$ alkyl) amine oxide, di($C_{12}$-$C_{14}$ alkyl) methyl amine oxide, di($C_{16}$-$C_{18}$ alkyl) methyl amine oxide, di($C_{20}$-$C_{22}$ alkyl) methyl amine oxide, di(tallow alkyl) methyl amine oxide, di(coco alkyl) methyl amine oxide.

9. Polyamide stabilizers, for example copper salts in combination with iodides and/or phosphorus compounds and salts of divalent manganese.

10. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

11. Nucleating agents, for example, 4-tert-butyl-benzoic acid, adipic acid, diphenylacetic acid.

12. Fillers and reinforcing agents, for example, calcium carbonate, silicates, glass fibers, asbestos, talc, kaolin, mica, barium sulfate, metal oxides and hydroxides, carbon black, graphite.

13. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

14. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzofuran-2-one, 5,7-di-tert-butyl-3-[4-(2-stearoyloxy-ethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 14, are added for example in concentrations of 0.01 to 10%, relative to the total weight of the material to be stabilized.

Further compositions comprise, in addition to components (a) and (b) further additives, such as phenolic antioxidants, light stabilizers or processing stabilizers.

These additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also the benzofuran-2-ones, such as described, for example, in U.S. Pat. Nos. 4,325,863, 4,338,244 or 5,175,312.

For examples, the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl] isocyanurate, 3,5-di-(3,5-di-tert-butyl-4-hydroxybenzyl) mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzyl-phosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

Another embodiment is the phenolic antioxidant which is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4hydroxybenzyl)isocyanurate, 2,6-di-tert-butyl-p-cresol or 2,2'-ethylidene-bis(4,6-di-tert-butylphenol).

The hindered amine compound is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl) ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetra-methylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl] 1,2,3,4-butanetetracarboxylate, mixed [1,2,2,6,6-pentamethylpiperidin-4-yl/β,β,β',β'-tetramethyl-3,9-(2,4 ,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl-n-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

Another hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetra-methylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1 cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The instant composition can additionally contain another UV absorber selected from the group consisting of the benzotriazoles, s-triazines, the oxanilides, the hydroxybenzophenones, benzoates and the α-cyanoacrylates.

The Instant composition may additionally contain an effective stabilizing amount of at least one other 2-hydroxyphenyl-2H-benzotriazole; another tris-aryl-s-triazine; or hindered amine or mixtures thereof.

The 2-hydroxyphenyl-2H-benzotriazole is selected from the group consisting of
2-(2-hydroxy-3,5-di-tert-amylphenyl)-2H-benzotriazole;
2-[2-hydroxy-3,5-di(α,α-dimethylbenzyl)phenyl]-2H-benzotriazole;
2-[2-hydroxy-3-(α,α-dimethylbenzyl)-5-tert-octylphenyl]-2H-benzotriazole;
2-{2-hydroxy-3-tert-butyl-5-[2-(omega-hydroxy-octa(ethyleneoxy)carbonyl)ethyl]-phenyl}-2H-benzotriazole;
5-chloro-2-(2-hydroxy-3,5-di-tert-butylphenyl)-2H-benzotriazole;
5-chloro-2-(2-hydroxy-3-tert-butyl-5-methylphenyl)-2H-benzotriazole;
2-(2-hydroxy-5-tert-octylphenyl)-2H-benzotriazole; and
2-(2-hydroxy-3-tert-butyl-5-[2-(octyloxy)carbonyl)ethyl] phenyl)-2H-benzotriazole.

The other tris-aryl-s-triazine is selected from the group consisting of
2,4-bis(2,4-dimethylphenyl)-6-(2-hydroxy-4-octyloxyphenyl)-s-triazine;
2,4-diphenyl-6-(2-hydroxy-4-hexyloxyphenyl)-s-triazine;
2,4-bis(2,4-dimethylphenyl)-6-[2-hydroxy-4-(3-do-/tridecyloxy-2-hydroxypropoxy)phenyl]-s-triazine; and
2-(2-hydroxyethylamino)-4,6-bis[N-butyl-N-(1-cyclohexyloxy-2,2,6,6-tetramethyl-piperidin-4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

The lacquers stabilized in accordance with the invention are suitable both for metal finish coatings and solid shade finishes, such as in the case of retouching finishes, as well as various coil coating applications. The lacquers stabilized in accordance with the invention are applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be espeically useful in other applications where their enhanced durability is required such as in solar films and the like.

Still another embodiment of the instant invention is a composition which comprises (a) candle wax which is white and scented, white and unscented, dyed and scented, dyed and unscented, dipped and scented or dipped and unscented, and (b) an effective stabilizing amount of a compound of formula I, II III, IV, V and/or VI as described above.

It should be noted that candles contain a host of various components. The base materials may be made up of the following:
  paraffin wax,
  natural oils,
  polyamide plus fatty acid/ester,
  fatty acids such as stearin,
  opacifiers,
  beeswax,
  glycerides plus oxidized wax,
  alcohols, and
  ethylene oligomers.

Candles also contain a number of additives such as the following:
  mold release agents,
  fragrances,
  insect repellants or insecticides,
  hardeners,
  crystal modifiers,
  clarifiers,
  guttering reducers,
  colorants,
  f.p. control agents,
  stretchability improvers,
  gelling agents,
  extrusion aids, and
  vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styrene-isoprene-styrene (SIS).

The following examples are for illustrative purposes only and are not to be construed to limit the scope of the invention in any manner whatsoever.

EXAMPLE 1

Compound 49:
1-Ethoxy-4-hydroxy-2,2,6,6-tetramethylpiperidine (1 mole Triethylborane/1.5 mole Silver Nitrate/3 mole Sodium Hydroxide)

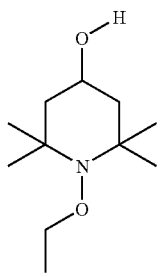

compound 49

Into a suspension of 2.15 g (12.5 mmol) of 4-hydroxy-2,2,6,6-tetramethyl-piperidine-1-oxyl, 1.50 g (37.5 mmol) of sodium hydroxide and 3.17 g (18.8 mmol) of silver nitrate in 30 mL of water at ambient temperature under nitrogen is added dropwise 12.5 mL (12.5 mmol) a 1M tetrahydrofuran solution of triethylborane. During addition, the temperature of the reaction mixture increases from 23° C. to 40° C. After addition, the reddish color of the reaction mixture becomes colorless. Thin layer chromatography (50% ethyl acetate/heptane) shows no starting material. The reaction mixture is then extracted with total of 40 mL of ethyl acetate and dried over anhydrous sodium sulfate. Filtration is used to remove inorganic solids and the filtrate is concentrated to a crude off-white oil. The crude product is purified by dry-column flash chromatography (20:80/ethyl acetate:heptane eluent) to give 1.90 g of an white crystalline solid in 75.7% yield: $^1$H NMR (CDCL$_3$) (300.08 MHz) δ 1.12 (t, CH$_3$, 3H, $^3J_{HH}$=7.00 Hz) 1.19 (s, CH$_3$, 6H), 1.15 (s, CH$_3$, 6H), 1.81, 1.58, 1.45 (overlapping m, CH$_2$, 4H), 3.78 (q, CH$_2$, 2H, $^3J_{HH}$=7.10Hz), 3.96 (m, CH, 1H), MS [M+1] 201.

Elemental Analysis: Calcd. for C$_{11}$H$_{23}$NO$_2$: C, 65.63; H, 11.16; N, 6.96 Found: C, 65.73; H, 11.16; N, 6.85

EXAMPLE 2

Compound 49:
1-Ethoxy-4-hydroxy-2,2,6,6-tetramethylpiperidine (0.3 mole Triethylborane/1.5 mole Silver Nitrate/3 mole Sodium Hydroxide)

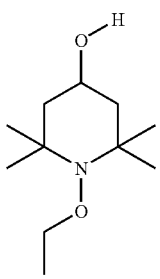

compound 49

The procedure of Example (1) is repeated using 2.15 g (12.5 mmol) of 4-hydroxy-2,2,6,6-tetramethyl-piperidine-1-oxyl, 1.50 g (37.5 mmol) of sodium hydroxide, 3.17 g (18.8 mmol) of silver nitrate and 4.2 mL (4.2 mmol) a 1M tetrahydrofuran solution of triethylborane in 30 mL of water at ambient temperature. The aforementioned work up gives 2.20 g of crude off-white solid in 87.6% yield.

EXAMPLE 3

Compound 49:
1-Ethoxy-4-hydroxy-2,2,6,6-tetramethylpiperidine (1 mole Triethylborane/5% mole Silver Nitrate/5% mole Copper(II) Acetate/3 mole Sodium Hydroxide/Static Oxygen)

Into a suspension of 2.15 g (12.5 mmol) of 4hydroxy-2,2,6,6-tetramethyl-piperidine-1-oxyl, 1.50 g (37.5 mmol) of sodium hydroxide, 110 mg (0.625 mmol) of silver nitrate and 120 mg (0.625 mmol) of copper (II) acetate monohydrate in 40 mL of water at ambient temperature and a static blanket of atmospheric oxygen is added dropwise 12.5 mL (12.5 mmol) a 1M tetrahydrofuran solution of triethylborane After stirring for 48 hours, no starting nitroxyl is detected by thin layer chromatography. The reaction mixture is then extracted with total of 40 mL of ethyl acetate and dried over anhydrous sodium sulfate. Filtration is used to remove inorganic and filtrate is concentrated to a crude off-white oil. The product is purified by dry-column flash chromatography (20:80/ethyl acetate:heptane eluent) to give 2.47 g of a white crystalline solid in 98.4% yield.

EXAMPLE 4

Compound 49:
1-Ethoxy-4-hydroxy-2,2,6,6-tetramethylpiperidine (1 mole Triethylborane/1% mole Silver Nitrate/5% mole Copper(II) Acetate/3 mole Sodium Hydroxide/Static Oxygen)

The procedure of Example (3) is repeated using 2.15 g (12.5 mmol) of 4-hydroxy-2,2,6,6-tetramethyl-piperidine-1-oxyl, 1.50 g (37.5 mmol) of sodium hydroxide, 21 mg (0.125 mmol) of silver nitrate and 120 mg (0.625 mmol) of copper (II) acetate monohydrate and 12.5 mL (12.5 mmol) a 1M tetrahydrofuran solution of triethylborane in 40 mL of water at ambient temperature and a static blanket of atmospheric oxygen. The product is purified by dry-column flash chromatography (20:80/ethyl acetate:heptane eluent) to give 2.45 g of a white crystalline solid in 97.6% yield.

EXAMPLE 5

Compound 49:
1-Ethoxy-4-hydroxy-2,2,6,6-tetramethylpiperidine (1 mole Triethylborane/1% mole Silver Nitrate/1% mole Copper(II) Acetate/3 mole Sodium Hydroxide/Static Oxygen)

The procedure of Example (3) is repeated using 2.15 g (12.5 mmol) of 4-hydroxy-2,2,6,6-tetramethyl-piperidine-1-oxyl, 1.50 g (37.5 mmol) of sodium hydroxide, 21 mg (0.125 mmol) of silver nitrate and 24 mg (0.125 mmol) of copper (II) acetate monohydrate and 12.5 mL (12.5 mmol) a 1M tetrahydrofuran solution of triethylborane in 40 mL of water at ambient temperature and a static blanket of atmospheric oxygen. The product is purified by dry-column flash chromatography (20:80/ethyl acetate:heptane eluent) to give 2.31 g of a white crystalline solid in 92.0% yield.

EXAMPLE 6

Compound 49:
1-Ethoxy-4-hydroxy-2,2,6,6-tetramethylpiperidine (1 mole Triethylborane/1% mole Silver Nitrate/5% Copper (II) Acetate/3 mole Sodium Hydroxide/Bubbling Air)

The procedure of Example (3) is repeated using 2.15 g (12.5 mmol) of 4-hydroxy-2,2,6,6-tetramethyl-piperidine-1-oxyl, 1.50g (37.5 mmol) of sodium hydroxide, 21 mg (0.125 mmol) of silver nitrate and 120 mg (0.625 mmol) of copper (II) acetate monohydrate and 12.5 mL (12.5 mmol) a 1M tetrahydrofuran solution of triethylborane in 40 mL of water at ambient temperature and a stream of air bubbling into the reaction mixture. No starting nitroxyl is detected after one hour. The product is purified by dry-column flash chromatography (20:80/ethyl acetate:heptane eluent) to give 2.40 g of a white crystalline solid in 95.6% yield.

EXAMPLE 7

Compound 49:
1-Ethoxy-4-hydroxy-2,2,6,6-tetramethylpiperidine (0.3 mole Triethylborane/1% mole Dilver Nitrate/5% mole Copper(II) Acetate/3 mole Sodium Hydroxide/Bubbling Air)

The procedure of Example (3) is repeated using 2.15 g (12.5 mmol) of 4-hydroxy-2,2,6,6-tetramethyl-piperidine-1-oxyl, 1.50 g (37.5 mmol) of sodium hydroxide, 21 mg (0.125 mmol) of silver nitrate and 120 mg (0.625 mmol) of copper (II) acetate monohydrate and 4.2 mL (4.2 mmol) a 1M tetrahydrofuran solution of triethylborane in 40 mL of water at ambient temperature and a stream of air bubbling into the reaction mixture. No starting nitroxyl is detected after one hour. The product is purified by dry-column flash chromatography (20:80/ethyl acetate:heptane eluent) to give 2.48 g of a white crystalline solid in 98.8% yield.

EXAMPLE 8

Compound 177:
1-Ethoxy-4-oxo-2,2,6,6-tetramethylpiperidine (1 mole Triethylborane/1.5 mole Silver Nitrate/3 mole Sodium Carbonate)

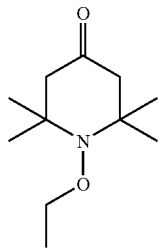

compound 177

The procedure of Example (1) is repeated using 2.12 g (12.5 mmol) of 4-oxo-2,2,6,6-tetramethyl-piperidine-1-oxyl, 3.91 g (37.5 mmol) of sodium carbonate and 3.17 g (18.8 mmol) of silver nitrate in 40 mL of water at ambient temperature under nitrogen is added dropwise 12.5 mL (12.5 mmol) a 1M tetrahydrofuran solution of triethylborane. The product is purified by dry-column flash chromatography (heptane eluent) to give 2.30 g of a white crystalline solid in 93.5% yield: $^1$H NMR (CDCL$_3$) (300.08 MHz) δ 1.15 (t, CH$_3$, 3H, $^3J_{HH'}$=7.10 Hz) 1.16 (s, CH$_3$, 6 H), 1.30 (s, CH$_3$, 6 H), 2.22 (d, CH$_2$, 2H, $^2J_{HH'}$=12.72 Hz), 2.55(d, CH$_2$, 2H, $^2J_{HH'}$=12.72 Hz) 3.87 (q, CH$_2$, 2H, $^3J_{HH'}$=7.10 Hz); MS [M+1] 200.

Elemental Analysis: Calcd. for C$_{11}$H$_{21}$NO$_2$: C, 66.29; H, 10.62; N, 7.03 Found: C, 66.14; H, 10.83; N, 6.89

EXAMPLE 9

Compound 177:
1-Ethoxy-4-oxo-2,2,6,6-tetramethylpiperidine (0.3 mole Triethylborane/1% mole Silver Nitrate/5% mole Copper(II) Acetate/3 mole Sodium Carbonate/Static Oxygen)

The procedure of Example (3) is repeated using 2.12 g (12.5 mmol) of 4-oxo-2,2,6,6-tetramethyl-piperidine-1-oxyl, 3.91 g (37.5 mmol) of sodium carbonate, 21 mg (0.125 mmol) of silver nitrate and 120 mg (0.625 mmol) of copper (II) acetate monohydrate and 12.5mL (12.5 mmol) a 1M tetrahydrofuran solution of triethylborane in 40 mL of water at ambient temperature and a static blanket of atmospheric oxygen. No starting nitroxyl is detected after one hour. The product is purified by dry-column flash chromatography (heptane eluent) to give 2.15 g of a white crystalline solid in 87.4% yield.

EXAMPLE 10

Compound 160/2: 1-Cyclohexyloxy-4-hydroxy-2,2,6,6-tetramethylpiperidine (1 mole Tricyclohexylborane 1.5 mole Silver Nitrate/3 mole Sodium Hydroxide)

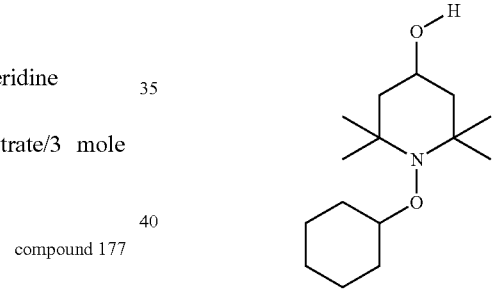

compound 160/2

Into a solution of 2.85 g (35 mmol) of cyclohexene in 20 mL of tetrahydrofuran at ambient temperature under nitrogen is added dropwise 12.5 mL (12.5 mmol) of a 1M tetrahydrofuran solution of borane. During addition, reaction temperature is kept under 35° C. Reaction mixture, after addition, is then heated to 40° C. for 2 hours. After cooled to ambient temperature, the reaction is added dropwise into a suspension of 2.15 g (12.5 mmol) of 4-hydroxy-2,2,6,6-tetramethyl-piperidine-1-oxyl, 1.50 g (37.5 mmol) of sodium hydroxide and 3.17 g (18.8 mmol) of silver nitrate in 40 mL of water at ambient temperature under nitrogen. Thin layer chromatography detects no more starting nitroxyl after 2 hours. Reaction mixture is extracted with 2×10 mL of ethyl acetate and dried over sodium sulfate. Filtration removes inorganic and filtrate is concentrated to an off-white oil. Purification of product by dry-column flash chromatography (20:80/ ethyl acetate:heptane eluent) gives 3.14 g of a white crystalline solid in 98.7% yield: $^1$H NMR (CDCL$_3$) (300.08 MHz)δ 1.15 (s, CH$_3$, 6 H), 1.20 (s, CH$_3$ ,6H), 1.22, 1.46 (m, CH$_2$, 4H), 1.76, 1.81 (m, CH$_2$, 10H)3.60 (m, CH, 1H),3.90 (m, CH, 1H); MS [M+1]256.

Elemental Analysis: Calcd. for C$_{15}$H$_{29}$NO$_2$: C, 70.54; H, 11.45; N, 5.48 Found: C, 69.85; H, 11.30; N, 5.22

EXAMPLE 11

Compound 180:
1-Butoxy-4-hydroxy-2,2,6,6-tetramethylpiperidine (0.3 mole Tributylborane/1% mole Silver Nitrate/5% mole Copper(II) Acetate/3 mole Sodium Hydroxide/Bubbling Air)

compound 180

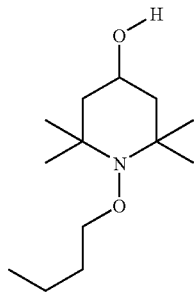

The procedure of Example (3) is repeated using 2.15 g (12.5 mmol) of 4-hydroxy-2,2,6,6-tetramethyl-piperidine-1-oxyl, 1.50 g (37.5 mmol) of sodium hydroxide, 21 mg (0.125 mmol) of silver nitrate and 120 mg (0.625 mmol) of copper (II) acetate monohydrate and 12.5 mL (12.5 mmol) a 1M tetrahydrofuran solution of triethylborane in 40 mL of water at ambient temperature and a stream of air bubbling into the reaction mixture; No starting nitroxyl is detected after one hour. The product is purified by dry-column flash chromatography (20:80/ethyl acetate:heptane eluent) to give 2.82 g of a white crystalline solid in 98.6% yield: MS [M+1]230.

EXAMPLE 12

Compound 181:
1-octyloxy-4-hydroxy-2,2,6,6-tetramethylpiperidine (1 mole Trioctylborane/1% mole Silver Nitrate/5% mole Copper(II) Acetate/3 mole Sodium Hydroxide)

compound 181

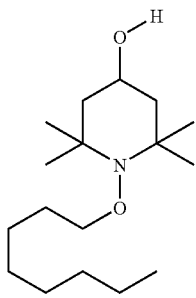

The procedure of Example (10) is repeated using 4.20 g (37.5 mmol) of 1-octene in 20 mL of tetrahydrofuran, 12.5 mL (12.5 mmol ) of 1M tetrahydrofuran solution of borane, 2.15 g (12.5 mmol) of 4-hydroxy-2,2,6,6-tetramethyl-piperidine-1-oxyl, 1.50 g (37.5 mmol) of sodium hydroxide, 21 mg (0.125 mmol) of silver nitrate and 120 mg (0.625 mmol) of copper (II) acetate monohydrate in 40 mL of water at ambient temperature and a static blanket of atmospheric oxygen. The product is purified by dry-column flash chromatography (20:80/ethyl acetate:heptane eluent) to give 3.40 g of a colorless oil in 94.3% yield : $^1$H NMR (CDCL$_3$) (300.08 MHz) δ 0.89 (t, CH$_3$, 3 H), 1.15 (s, CH$_3$, 6 H),1.20 (s, CH$_3$, 6H), 1.28(m, CH$_2$, 10H), 1.45 (m, CH$_2$, 2H), 1.49 (m, CH$_2$, 2 H), 1.80 (m, CH$_2$, 2H),3.72 (t, CH$_2$, 2H, $^3J_{HH'}$=6.53 Hz), 3.96 (m, CH, 1H); MS [M+1]286.

Elemental Analysis: Calcd. for C$_{17}$H$_{35}$NO$_2$: C,71.53; H, 12.36; N, 4.91 Found: C, 71.23; H, 12.35; N, 4.67

EXAMPLE 13

Compound 178:
1-alkyloxy-4-hydroxy-2,2,6,6-tetramethylpiperidine (1 mole Tri-alkylborane/1.5% mole Silver Nitrate/3 mole Sodium Hydroxide)

Alkyl is a Mixture of Alpha Olefins Range from C16 to C18 (Average C17)

The procedure of Example (10) is repeated using 8.90 g (37.5 mmol) of a mixture of alpha olefins range from C16 to C18 (average C17 ) in 20 mL of tetrahydrofuran, 12.5 mL (12.5 mmol) of 1M tetrahydrofuran solution of borane, 2.15 g (12.5 mmol) of 4-hydroxy-2,2,6,6-tetramethyl-piperidine-1-oxyl, 1.50 g (37.5 mmol) of sodium hydroxide and 3.17 mg (18.8 mmol) of silver nitrate in 50 mL of water at ambient temperature under nitrogen. The product is purified by dry-column flash chromatography (10:90/ethyl acetate:heptane eluent) to give 4.95 g of a colorless oil in 96.5% yield.

EXAMPLE 14

Compound 179: 1-alkyoxy-4-hydroxy-2,2,6,6-tetramethylpiperidinyl-1-oxyl (1 mole Tri-alkylborane/1.5% mole Silver Nitrate/3 mole Sodium Hydroxide)

Alkyl is a Mixture of Alpha Olefins Range from C18 to C30 (Average C22)

The procedure of Example (10) is repeated using 11.55 g (37.5 mmol) of a mixture of alpha olefins range from C18 to C30 (average C22) in 20 mL of tetrahydrofuran,12.5 mL (12.5 mmol) of 1M tetrahydrofuran solution of borane, 2.15 g (12.5 mmol) of 4-hydroxy-2,2,6,6-tetramethyl-piperidine-1-oxyl, 1.50 g (37.5 mmol) of sodium hydroxide and 3.17 mg (18.8 mmol) of silver nitrate in 50 mL of water at ambient temperature under nitrogen. The product is purified by dry-column flash chromatography (10:90/ethyl acetate:heptane eluent) to give 4.80 g of a colorless oil in 80.0% yield.

EXAMPLE 15

1-Ethoxyl-4-acetoamido-2,2,6,6-tetramethylpiperidine

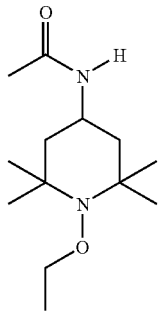

The procedure of Example (1) is repeated using 2.66 g (12.5 mmol) of 4-acetoamido-2,2,6,6-tetramethyl-piperidine-1-oxyl, 1.50 g (37.5 mmol) of sodium hydroxide, 3.17 g (18.8 mmol) of silver nitrate and 12.5 mL (12.5 mmol) a 1M tetrahydrofuran solution of triethylborane in 40 mL of water at ambient temperature. The aforementioned work up gives 2.20 g of crude off-white solid in 97.7% yield: $^1$H NMR (CDCL$_3$) (300.08 MHz) δ 1.11 (t, CH$_3$, 3H, $^3J_{HH}$=7.10 Hz), 1.17 (s, CH$_3$, 6 H), 1.19 (s, CH$_3$, 6H),1.30, 1.75 (m, CH$_2$, 4H), 1.95(s, CH$_3$, 3H),3.76 (q, CH$_2$, 2H, $^3J_{HH}$=7.17Hz), 4.13 (m, CH, 1H), 5.15 (b, NH, 1H); MS [M+1]243.

EXAMPLE 16

1-Ethoxyl-2,5-diethyl-2,5-dimethyl-imidazolidin-4-one

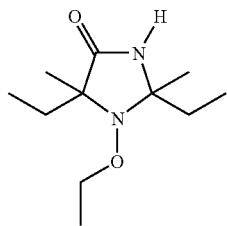

The procedure of Example (1) is repeated using 2.31 g (12.5 mmol) of 2,5-diethyl-2,5-dimethyl-imidazolidin-4-one-1-oxyl, 1.50 g (37.5 mmol) of sodium hydroxide, 3.17 g (18.8 mmol) of silver nitrate and 12.5 mL (12.5 mmol) a 1M tetrahydrofuran solution of triethylborane in 40 mL of water at ambient temperature. The aforementioned work up gives 2.42 g of crude off-white solid in 90.6% yield: $^1$H NMR (CDCL$_3$) (300.08 MHz)δ 0.97 (t, CH$_3$, 6H),1.18 (t, CH$_3$, 3 H), 1.34 (s, CH$_3$, 3H), 1.42 (s, CH$_3$, 3H),1.61, 1.71 (m, CH$_2$, 4H ),3.83 (q, CH$_2$, 2H), 5.53 (b, NH, 1H); MS [M+1]215.

Elemental Analysis: Calcd. for C$_{11}$H$_{22}$N$_2$O$_2$: C, 61.65; H, 10.35; N, 13.07 Found: C, 61.63; H, 10.07; N, 12.64

What is claimed is:

1. A process for preparing a sterically hindered amine of formula I, II, III, IV, V or VI (I)

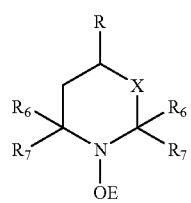

(II)

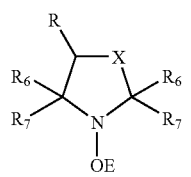

(III)

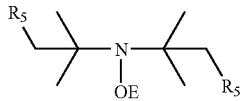

-continued (IV)

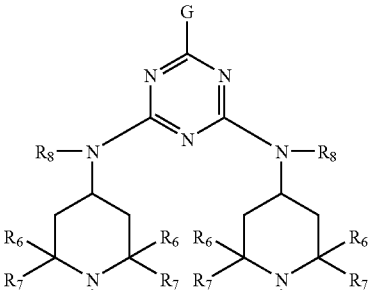

(V)

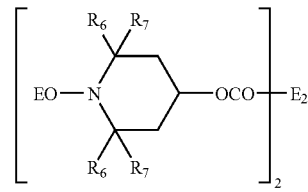

(VI)

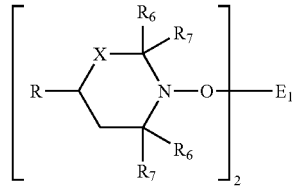

which process comprises reacting a corresponding sterically hindered nitroxyl compound of formula Ia, IIa, IIIa, IVa or Va (Ia)

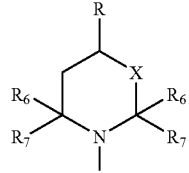

(IIa)

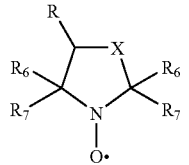

(IIIa)

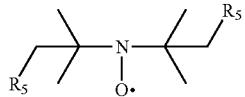

(IVa)

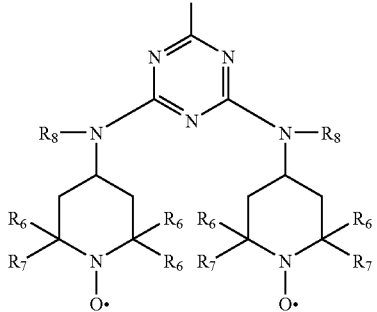

-continued

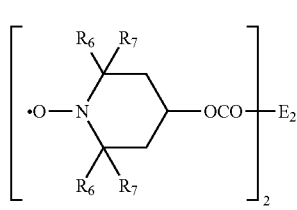

(Va)

with an alkylborane of formula

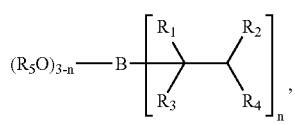

or reacting two equivalents of the sterically hindered nitroxyl of formula Ia with a cyclic or bis alkylborane of formula

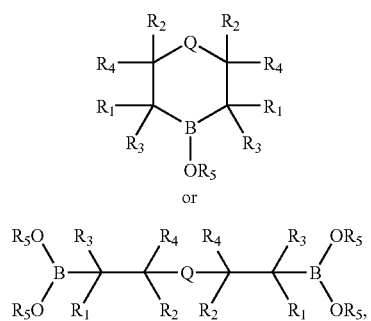

in the presence of silver,
wherein

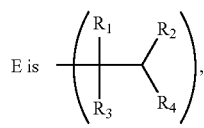

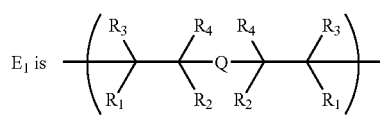

n is 1 to 3,

R is hydrogen, alkyl of 1 to 18 carbon atoms, aralky of 7 to 15 carbon atoms, aryl of 6 to 10 carbon atoms, hydroxyl, carboxyl, amino, alkylamino of 1 to 18 carbon atoms, dialkylamino of 2 to 36 carbon atoms, oxo, alkylthio of 1 to 18 carbon atoms, alkoxy of 1 to 18 carbon atoms, aryloxy of 7 to 15 carbon atoms, benzoyloxy, alkylcarbonyloxy of 2 to 18 carbon atoms or alkylcarbonylamino of 2 to 18 carbon atoms, $R_1$ to $R_4$ are independently hydrogen, halogen, alkyl of 1 to 18 carbon atoms, aralkyl of 7 to 15 carbon atoms, aryl of 6 to 10 carbon atoms, alkylthio of 1 to 18 carbon atoms, alkoxy of 1 to 18 carbon atoms, aryloxy of 7 to 15 carbon atoms, or $R_1$ and $R_2$ together with the carbon atoms to which they are attached form a cycloalkylene of 5 to 18 carbon atoms or said cycloalkylene interrupted by 1 to 3 nitrogen, oxygen or sulfur atoms; or said cycloalkylene substituted by 1 to 3 halogen, alkyl of 1 to 18 carbon atoms, aralkyl of 7 to 15 carbon atoms, aryl of 6 to 10 carbon atoms, alkylthio of 1 to 18 carbon atoms, alkoxy of 1 to 18 carbon atoms or aryloxy of 7 to 15 carbon atoms, $R_5$ is hydrogen, alkyl of 1 to 18 carbon atoms, cycloalkyl of 5 to 12 carbon atoms, aralkyl of 7 to 15 carbon atoms or aryl of 6 to 10 carbon atoms, $R_6$ and $R_7$ are independently alkyl of 1 to 8 carbon atoms, or $R_6$ and $R_7$ together are tetramethylene or pentamethylene, X is —$CH_2$—, —O—, —S—, or —$NR_8$—, $R_8$ is hydrogen or alkyl of 1 to 12 carbon atoms, Q is a direct bond or is methylene of 1 to 12 carbon atoms or said methylene interrupted by 1 or 2 nitrogen, oxygen or sulfur atoms, $E_2$ is alkylene of 2 to 12 carbon atoms and G is chloro or —N(2-ethylhexyl)$_2$, wherein the silver is present in a catalytic amount and together with a Cu(II)/oxygen co-catalyst.

2. A process according to claim 1 wherein X is methylene.

3. A process according to claim 1 wherein R is hydrogen, hydroxyl, oxo or acetamido;

$R_1$ to $R_4$ are each hydrogen, or alkyl of 1 to 18 carbon atoms; or $R_1$ and $R_2$ together with the carbon atoms to which they are attached to form a cyclohexylene;

and $R_6$ and $R_7$ are each methyl or ethyl.

4. A process according to claim 1 where the sterically hindered amine is 1-octyloxy-4-hydroxy-2,2,6,6-tetramethylpiperidine, 1-ethoxyl-2,5-diethyl-2,5-dimethyl-imidazolidin-4-one, 1-butoxy-4-hydroxy-2,2,6,6-tetramethylpiperidine, 1-C18 to C30 alkyoxy-4-hydroxy-2,2,6,6-tetramethylpiperidinyl or 1-C16-C18alkyloxy-4-hydroxy-2,2,6,6-tetramethylpiperidine.

5. A process according to claim 1 where a the copper (II)/oxygen co-catalyst comprises copper (II) acetate or copper (II) sulfate.

6. A process as in claim 5 where oxygen is introduced as atomspheric oxygen or a mixture of oxygen with another inert gas or gases.

7. A process according to claim 1 wherein a solvent is used selected from water, a mixture of water and tetrahydrofuran, alcohol, a mixture of alcohol and tetrahydrofuran and a mixture of water and an alcohol.

8. A process according to claim 1 carried out between 0 and 100 degrees centigrade.

9. A process according to claim 1 where the catalytic amount of silver is 0.1 to 5 mole percent of the sterically hindered nitroxyl compound.

* * * * *